US010034493B2

(12) United States Patent
Akiyama et al.

(10) Patent No.: US 10,034,493 B2
(45) Date of Patent: Jul. 31, 2018

(54) PACKAGE FOR HOUSING A HEAT SOURCE

(71) Applicant: JAPAN TOBACCO INC., Tokyo (JP)

(72) Inventors: Takeshi Akiyama, Tokyo (JP); Manabu Yamada, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 335 days.

(21) Appl. No.: 14/845,043

(22) Filed: Sep. 3, 2015

(65) Prior Publication Data

US 2015/0374038 A1 Dec. 31, 2015

Related U.S. Application Data

(63) Continuation of application No. PCT/JP2014/055272, filed on Mar. 3, 2014.

(30) Foreign Application Priority Data

Mar. 8, 2013 (JP) ................................. 2013-047282

(51) Int. Cl.
*A24F 47/00* (2006.01)
*A61M 15/06* (2006.01)
(Continued)

(52) U.S. Cl.
CPC ......... *A24F 47/006* (2013.01); *A61M 11/048* (2014.02); *A61M 15/06* (2013.01);
(Continued)

(58) Field of Classification Search
None
See application file for complete search history.

(56) References Cited

U.S. PATENT DOCUMENTS 5,240,012 A 8/1993 Ehrman et al.
8,616,217 B2 12/2013 Tsurizumi et al.
(Continued)

FOREIGN PATENT DOCUMENTS

GB 1 473 675 A 5/1977
JP 50-25800 3/1975
(Continued)

OTHER PUBLICATIONS

Office Action issued in corresponding Japanese Application No. 2015-504293 dated May 24, 2016 (with English translation).
(Continued)

*Primary Examiner* — Alison L Hindenlang
*Assistant Examiner* — Jamel M Nelson
(74) *Attorney, Agent, or Firm* — Birch, Stewart, Kolasch & Birch, LLP

(57) ABSTRACT

A package for housing at least a heat source, used for a flavor inhaler, having a columnar shape extending along a predetermined direction and four housing a tubular member having a tubular shape. The package includes a bottom surface and a heat source holder for holding the heat source so that the predetermined direction is directed toward a direction crossing the bottom surface. The heat source holder holds the heat source provided separately of a tubular member and holds the heat source at a state that allows the heat source to swing toward the bottom surface, the tubular member, used for the flavor inhaler, having a tubular shape.

10 Claims, 8 Drawing Sheets

(51) Int. Cl.
  *B65D 25/10* (2006.01)
  *A61M 11/04* (2006.01)
  *B65D 85/10* (2006.01)
  *B65D 25/04* (2006.01)

(52) U.S. Cl.
  CPC ....... *B65D 25/101* (2013.01); *B65D 85/1036* (2013.01); *B65D 85/1081* (2013.01); *A61M 2205/3653* (2013.01); *B65D 25/04* (2013.01); *B65D 85/109* (2013.01)

(56) References Cited

U.S. PATENT DOCUMENTS

| | | |
|---|---|---|
| 8,776,803 B2 | 7/2014 | Tarora et al. |
| 2007/0215168 A1 | 9/2007 | Banerjee et al. |
| 2010/0258139 A1* | 10/2010 | Onishi ................ A24B 15/165 131/194 |
| 2013/0019888 A1 | 1/2013 | Tsuruizumi et al. |

FOREIGN PATENT DOCUMENTS

| | | | |
|---|---|---|---|
| JP | 2009-529872 A | 8/2009 | |
| JP | 4737779 B2 | 8/2011 | |
| JP | 2012-34602 A | 2/2012 | |
| WO | WO 2011/118024 A1 | 9/2011 | |
| WO | WO-2011118024 A1 * | 9/2011 | ........... A24B 15/165 |
| WO | WO 2012/171636 A1 | 12/2012 | |
| WO | WO-2012171636 A1 * | 12/2012 | ........... B65D 5/5213 |

OTHER PUBLICATIONS

International Search Report, issued in PCT/JP2014/055272, dated Jun. 3, 2014.
Extended European Search Report, dated Nov. 22, 2016, for European Application No. 14760293.2.
Japanese Office Action, dated Dec. 13, 2016, for Japanese Application No. 2015-504293, together with an English translation thereof.
European Office Action dated July 25, 2017, for corresponding European Application No. 14760293.2.

* cited by examiner

PACKAGE FOR HOUSING A HEAT SOURCE

CROSS REFERENCE TO RELATED APPLICATIONS

This application is a Continuation of PCT International Application No. PCT/JP2014/055272, filed on Mar. 3, 2014, which claims priority under 35 U.S.C. 119(a) to Patent Application No. 2013-047282, filed in Japan on Mar. 8, 2013, all of which are hereby expressly incorporated by reference into the present application.

TECHNICAL FIELD

The present invention relates to a package that houses at least a heat source configuring a flavor inhaler.

BACKGROUND ART

Conventionally, a flavor inhaler that includes a heat source having a columnar shape and a tubular member having a tubular shape is known. For example, one end portion of the tubular member configures a mouthpiece, and the other end portion of the tubular member configures a supporting end portion that supports the heat source. The heat source is a rod-shaped smoking article such as a cigarette and a cigar (for example, Patent Literature 1).

Further, there is also proposed a flavor inhaler that has a heat source as a heat source provided separately of the tubular member (for example, Patent Literature 2).

As described above, the flavor inhaler having a heat source and a tubular member as a separate body is proposed. However, there is no consideration to a configuration necessary for easily inserting the heat source provided separately of the tubular member into the tubular member. However, a heat source such as a carbon heat source applied to the flavor inhaler generally is small, that is, 1 cm$^3$ or less, and an operation of appropriately inserting such a small heat source into a tubular member that has an insertion opening approximately the same in dimension as the heat source is very troublesome for a user.

CITATION LIST

Patent Literature

[Patent Literature 1] U.S. Pat. No. 4,737,779
[Patent Literature 2] U.S. Pat. No. 5,240,012

SUMMARY

A package according to a first feature houses a heat source having a columnar shape extending along a predetermined direction and houses a tubular member having a tubular shape. The package comprises a bottom surface and a heat source holder holding the heat source so that the predetermined direction is directed toward a direction crossing the bottom surface.

In the first feature, the package comprises a partition member erected from the bottom surface. The partition member partitions a space within the package into a first space housing the heat source and a second space housing the tubular member. The heat source holder is formed in the first space.

In the first feature, one end portion of the heat source is a non-insertion end portion and the other end portion of the heat source is an insertion end portion inserted into the tubular member along the predetermined direction. The heat source holder has a structure to hold the heat source so that the insertion end portion protrudes from an upper end of the heat source holder.

In the first feature, the insertion end portion has an inclination surface having an inclination relative to the predetermined direction.

In the first feature, a length with which the insertion end portion protrudes from the upper end of the heat source holder is approximately equal to a length with which the insertion end portion should be inserted into the tubular member.

In the first feature, the heat source is a carbon heat source.
In the first feature, the heat source is a tobacco compact.
In the first feature, one end portion of the tubular member is a mouthpiece side end portion provided at a mouthpiece side and the other end portion of the tubular member is a supporting end portion that supports the heat source. The supporting end portion has a shape that an internal dimension of the supporting end portion decreases from the supporting end portion toward the mouthpiece side end portion.

In the first feature, one end portion of the heat source is a non-insertion end portion and the other end portion of the heat source is an insertion end portion inserted into the tubular member along the predetermined direction. One end portion of the tubular member is a mouthpiece side end portion provided at a mouthpiece side and the other end portion of the tubular member is a supporting end portion that supports the heat source. An inner wall of the supporting end portion has a regulation portion that regulates insertion of the insertion end portion along the predetermined direction.

A package according to a second feature houses at least a heat source having a columnar shape extending along a predetermined direction. The package comprises a bottom surface and a heat source holder holding the heat source so that the predetermined direction is directed toward a direction crossing the bottom surface.

DESCRIPTION OF EMBODIMENTS

Figure 1:
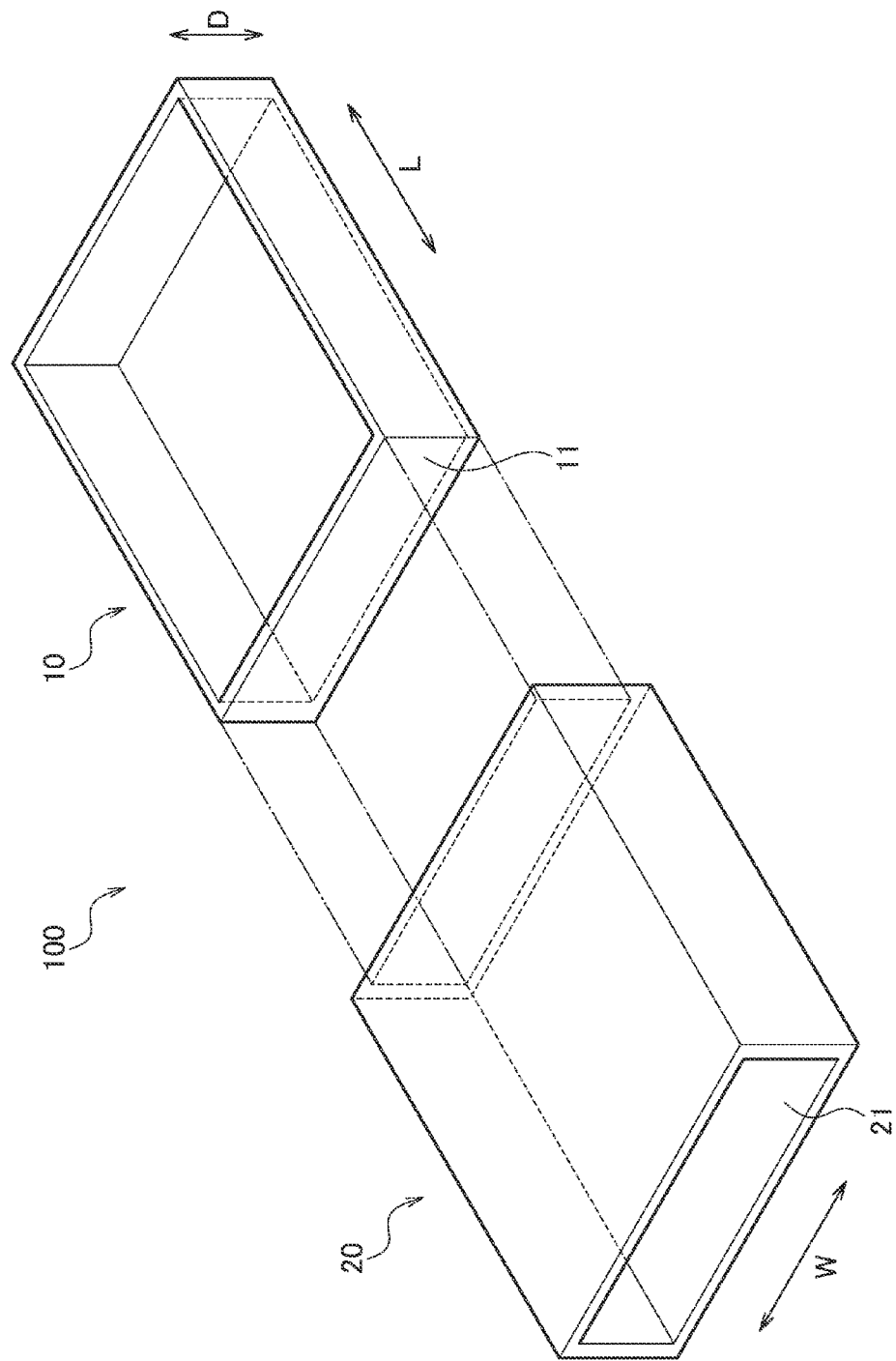
FIG. 1 is a schematic drawing showing a package 100 according to a first embodiment.

Hereinafter, the embodiments of the present invention will be described with reference to the drawings. In the following drawings, identical or similar components are denoted by identical or similar reference numerals.

Therefore, specific dimensions should be determined with reference to the description below. It is needless to mention that different relationships and ratio of dimensions may be included in different drawings.

SUMMARY OF EMBODIMENT

A package according to an embodiment houses a heat source having a columnar shape extending along a predetermined direction and houses a tubular member having a tubular shape. The package comprises a bottom surface and a heat source holder holding the heat source so that the predetermined direction is directed toward a direction crossing the bottom surface.

In an embodiment, the heat source holder holds the heat source so that the predetermined direction is directed toward the direction crossing the bottom surface. Therefore, it is possible to easily insert the heat source provided separately of a tubular member into the tubular member. In the embodiment, the predetermined direction is a direction from a non-insertion end portion of the heat source toward an insertion end portion thereof, for example. The insertion end portion of the heat source is an end portion inserted into the tubular member.

The direction crossing the bottom surface may be a vertical direction relative to the bottom surface. Alternatively, the direction crossing the bottom surface may have a predetermined inclination angle from the vertical direction relative to the bottom surface. The predetermined inclination angle is preferably 3 degrees or more and less than 90 degrees.

First Embodiment (Package)

A package according to a first embodiment will be described, below. FIG. 1 is a schematic drawing showing a package 100 according to the first embodiment.

As shown in FIG. 1, the package 100 has an inner case 10 and an outer case 20.

The inner case 10 has an approximately rectangular parallelepiped outer shape defined by a widthwise direction W, a longitudinal direction L and a depth direction D. The inner case 10 has a bottom surface 11 defined by the widthwise direction W and the longitudinal direction L. The inner case 10 has a box-like shape opening toward the opposite side of the bottom surface 11. For example, the inner case 10 is configured by a member (paper) having flexibility. The inner case 10 will be described in detail later (see FIG. 2).

The outer case 20 has an approximately rectangular parallelepiped outer shape defined by the widthwise direction W, the longitudinal direction L and the depth direction D. The outer case 20 has a tubular shape having a hollow 21 extending along the longitudinal direction L. The external dimension of the above-described inner case 10 is almost the same as the internal dimension of the hollow 21, and the inner case 10 is housed in the hollow 21 of the outer case 20.

For example, the outer case 20 is configured by a member (paper) having flexibility. It is needless to say that various types of materials including not only a member (paper) having flexibility but also resin and metal, for example, may be employed for the package.

(Inner Case)

Figure 2:
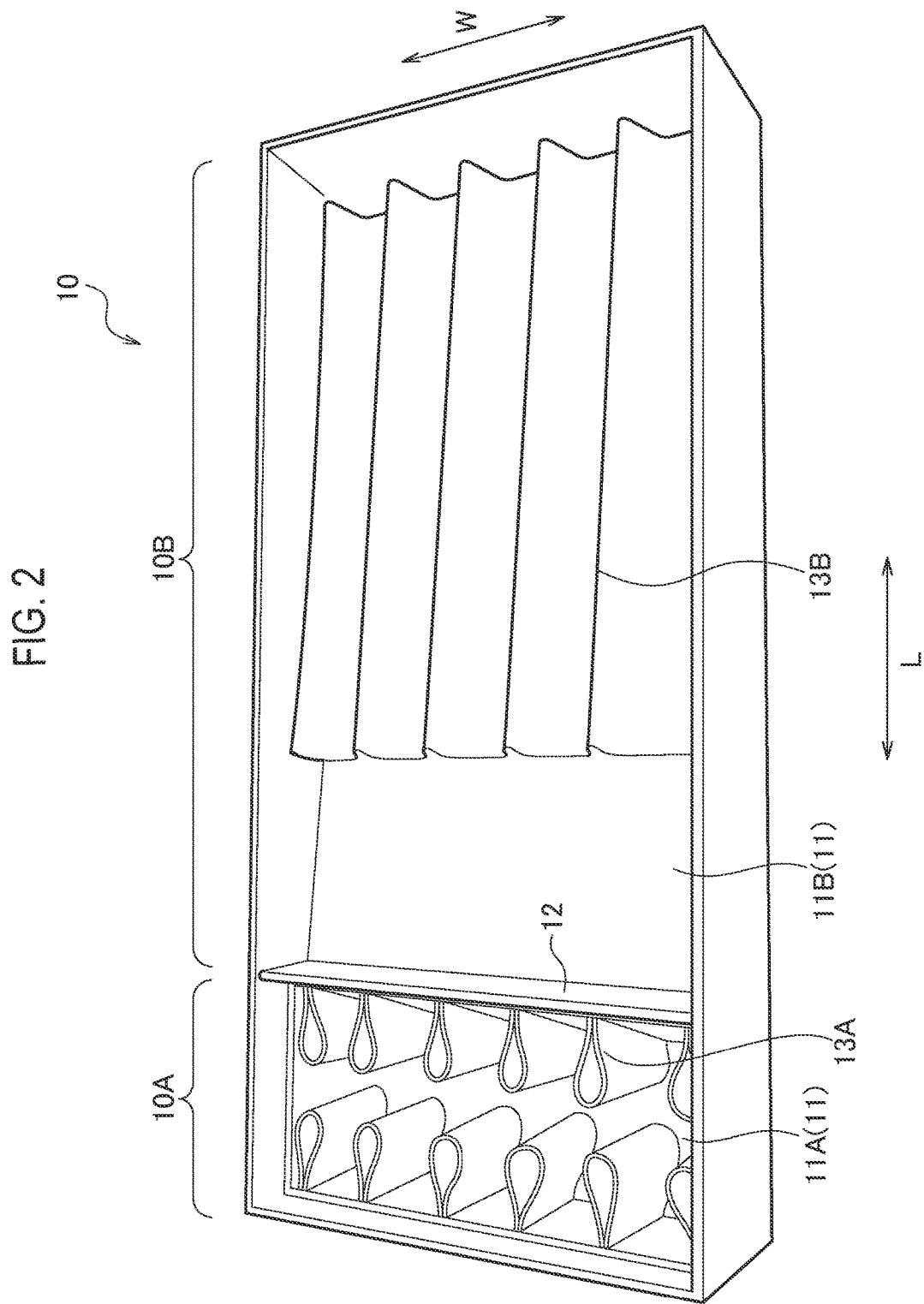
FIG. 2 is a schematic drawing showing an inner case 10 according to the first embodiment.

An inner case according to the first embodiment will be described, below. FIG. 2 is a schematic drawing showing an inner case 10 according to the first embodiment.

As shown in FIG. 2, the inner case 10 has a partition member 12 erected from the bottom surface 11. Specifically, the inner case 10 has a shape erected along the depth direction D. The partition member 12 partitions a space in the inner case 10 into a heat source housing space 10A (first space) housing a heat source and a tubular member housing space 10B (second space) housing a tubular member.

The heat source housing space 10A has a bottom surface 11A, as the bottom surface 11, on which a heat source is to be placed. The bottom surface 11A is approximately parallel to a plane defined by the widthwise direction W and the longitudinal direction L. The heat source housing space 10A has a heat source holder 13A that holds a heat source. The heat source holder 13A holds the heat source so that a predetermined direction is directed toward a direction (for example, a vertical direction (depth direction D) relative to the bottom surface 11A) crossing the bottom surface 11A.

The predetermined direction is a direction from a non-insertion end portion toward an insertion end portion of the heat source, for example. The insertion end portion of the heat source is an end portion inserted into the tubular member. In particular, the heat source holder 13A preferably holds the heat source so that the direction from the non-insertion end portion toward the insertion end portion of the heat source is directed toward a direction from the bottom surface 11A toward an opening. As a result, it is possible to easily insert the heat source into the tubular member with a state where the heat source is held by the heat source holder 13A. It is noted that holding the heat source does not require the heat source holder 13A to be in contact with the heat source, and the heat source holder 13A may be provided at a fixed interval with the heat source. In such a case, the heat source holder 13A restrains the heat source, which is placed on the bottom surface 11A, from being falling down.

As described above, when the inner case 10, in particular, the heat source holder 13A, is configured by a member (paper) having flexibility, it is easy to arrange the heat source within the inner case 10 and hold the heat source by the heat source holder 13A, and also to take out the heat source by inserting the heat source into the tubular member.

The tubular member housing space 10B has a bottom surface 11B, as the bottom surface 11, on which the tubular member should be placed. The bottom surface 11B may have an inclination relative to the plane defined by the widthwise direction W and the longitudinal direction L, as described later. The tubular member housing space 10B has a tubular member holder 13B that holds the tubular member. The tubular member holder 13B holds the tubular member in a state where the tubular member is laid on its side along the longitudinal direction L.

(Tubular Member)

Figure 3:
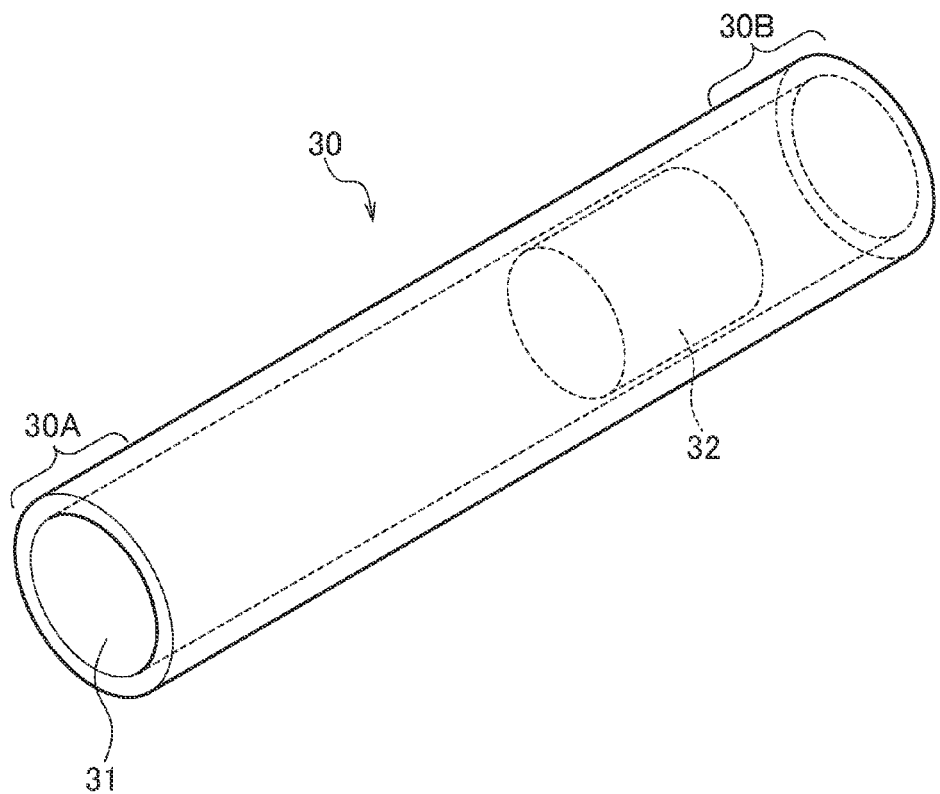
FIG. 3 is a schematic drawing showing a tubular member 30 according to the first embodiment.

The tubular member according to the first embodiment will be described, below. FIG. 3 is a schematic drawing showing the tubular member 30 according to the first embodiment.

As shown in FIG. 3, the tubular member 30 has a supporting end portion 30A and a mouthpiece side end portion 30B. The supporting end portion 30A is an end portion that holds the heat source. The mouthpiece side end portion 30B is an end portion provided at a mouthpiece side of a flavor inhaler. In the first embodiment, the mouthpiece side end portion 30B configures a mouthpiece of the flavor inhaler. However, the mouthpiece of the flavor inhaler may be provided separately of the tubular member 30.

The tubular member 30 has a tubular shape including a hollow 31 extending along a direction from the supporting end portion 30A toward the mouthpiece side end portion 30B. For example, the tubular member 30 has a tubular shape or a rectangular tubular shape. The tubular member 30 may have a flavor source such as a powdery and granular tobacco leaf used for a cigarette and a snuff and a tobacco compact, or a member 32 such as a filter. Moreover, as the flavor source, various flavor ingredients such as menthol may be supported in a support made of a porous material such as activated carbon or a non-porous material.

(Heat Source)

Figure 4:
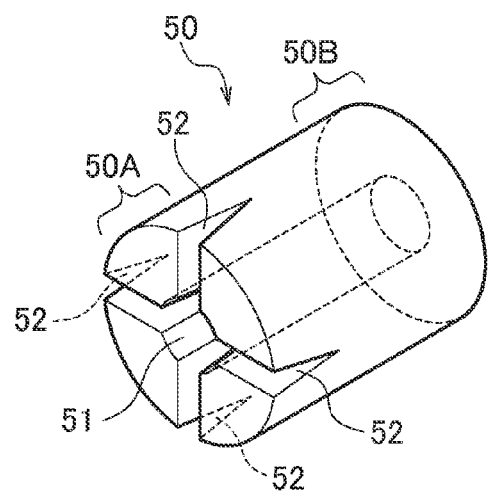
FIG. 4 is a schematic drawing showing a heat source 50 according to the first embodiment.

The heat source according to the first embodiment will be described, below. FIG. 4 is a schematic drawing showing the heat source 50 according to the first embodiment.

As shown in FIG. 4, the heat source 50 has a non-insertion end portion 50A and an insertion end portion 50B. The non-insertion end portion 50A is an end portion exposed from the tubular member 30 in a state where the heat source 50 is inserted into the tubular member 30. The insertion end portion 50B is an end portion inserted into the tubular member 30.

The heat source 50 has a columnar shape extending along a predetermined direction from the non-insertion end portion 50A toward the insertion end portion 50B. For example, the heat source 50 has a cylindrical shape or a rectangular tubular shape.

In the first embodiment, the heat source 50 is a combustion body such as a carbon heat source or a tobacco compact. However, the heat source 50 is not limited to a combustion body, and may be latent heat storage material that uses a latent heat (crystallization heat). Examples of the latent heat storage material may include sodium acetate trihydrate, sodium sulfate decahydrate, or magnesium nitrate hexahydrate.

In the first embodiment, the heat source 50 is a combustion body, and thus, the non-insertion end portion 50A configures an ignition end portion. The heat source 50 has a hollow 51 extending along a predetermined direction from the non-insertion end portion 50A toward the insertion end portion 50B. Because of the hollow 51, even in the inhalation (puff) in the latter half, it is possible to restrain variation in a heat amount supplied in the puff performed from ignition to extinction and to ensure a stable heat amount. The non-insertion end portion 50A and the insertion end portion 50B may have the same composition or shape, and may have a different composition or shape. For example, the non-insertion end portion 50A may have a notch 52 in communication with the hollow 51 to facilitate ignition of the heat source 50. Even when the non-insertion end portion 50A and the insertion end portion 50B have a different composition or shape, it is possible to hold the heat source 50 in the heat source housing space 10A while the heat source 50 previously is directed toward the predetermined direction, and thus, it is possible to prevent a user from inserting the heat source 50 in a wrong direction.

(Housing State of Heat Source and Tubular Member)

A housing state of the heat source and the tubular member according to the first embodiment will be described, below.

Figure 5:
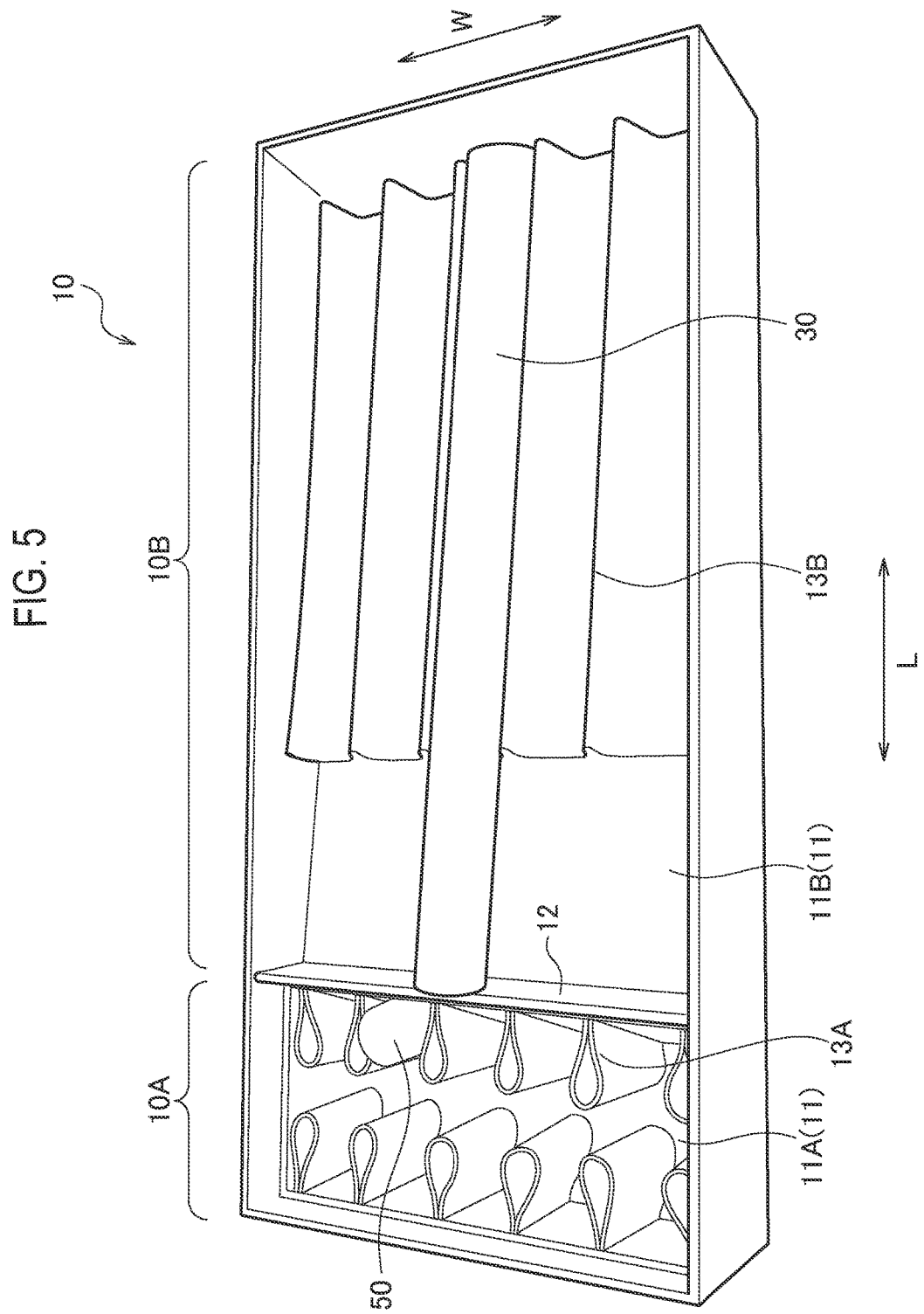
FIG. 5 is a drawing showing a housing state of a heat source 50 and a tubular member 30 according to the first embodiment.
Figure 6:
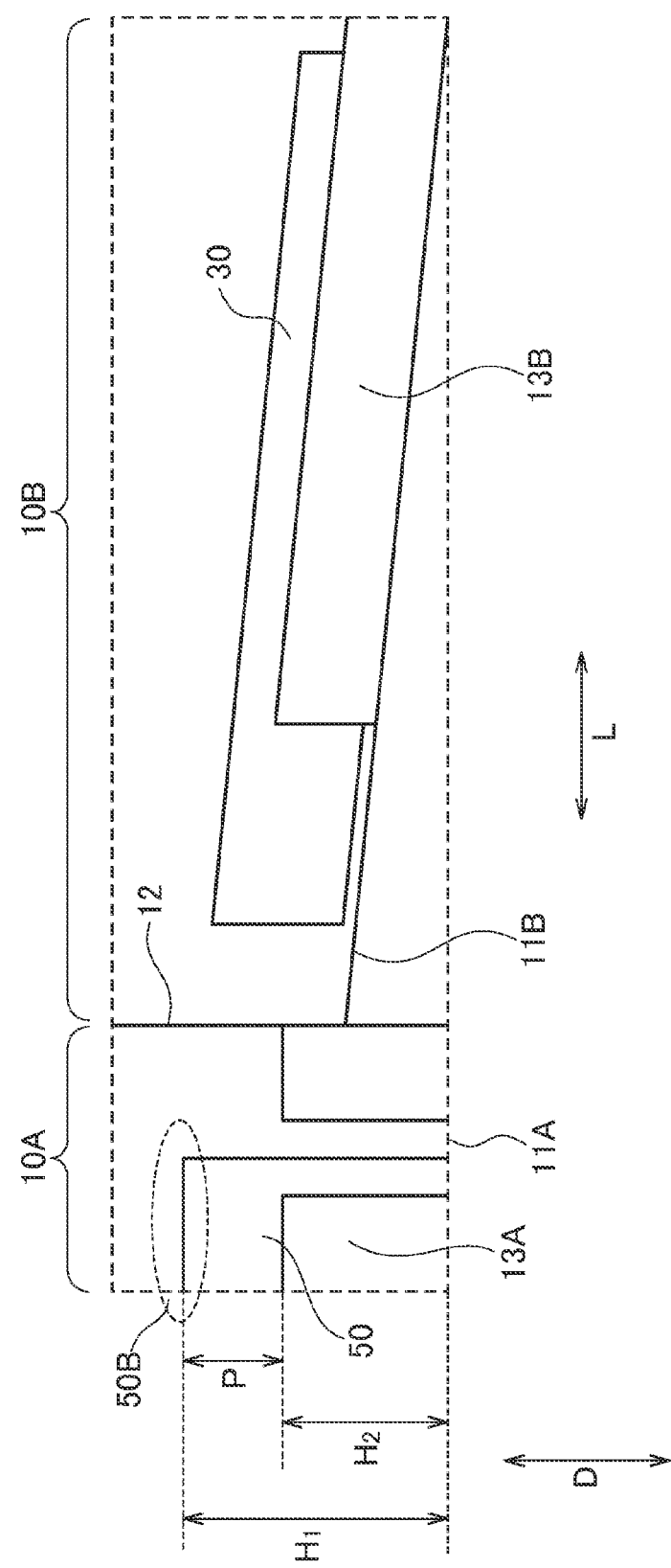
FIG. 6 is a drawing showing a housing state of a heat source 50 and a tubular member 30 according to the first embodiment.

FIG. 5 and FIG. 6 are drawings showing the housing state of the heat source 50 and the tubular member 30 according to the first embodiment.

As shown in FIG. 5 and FIG. 6, the heat source 50 is arranged in the heat source housing space 10A partitioned by the partition member 12. The heat source 50 is held by the heat source holder 13A so that the predetermined direction is directed toward a direction (for example, the depth direction D) crossing the bottom surface 11A, as described above. In particular, the heat source 50 is held so that the insertion end portion 50B faces the opposite side of the bottom surface 11A.

Here, the heat source holder 13A preferably has a structure to hold the heat source 50 so that the insertion end portion 50B protrudes from an upper end of the heat source holder 13A. A length with which the insertion end portion 50B of the heat source 50 protrudes from the upper end of the heat source holder 13A is preferably approximately equal to a length with which the insertion end portion 50B of the heat source 50 should be inserted into the tubular member 30.

In the first embodiment, a height H1 of the heat source 50 is greater than a height H2 of the heat source holder 13A in the depth direction D. A difference P between the height H1 and the height H2 is approximately equal to the length with which the insertion end portion 50B should be inserted into the tubular member 30. The height H1 is a length of the heat source 50 in the predetermined direction from the non-insertion end portion 50A toward the insertion end portion 50B. The difference P is a length with which the insertion end portion 50B protrudes from the upper end of the heat source holder 13A.

As shown in FIG. 5 and FIG. 6, the tubular member 30 is arranged in the tubular member housing space 10B partitioned by the partition member 12. As described above, the tubular member 30 is held by the tubular member holder 13B in a state where the tubular member 30 is laid on its side along the longitudinal direction L.

In the first embodiment, the bottom surface 11B may be inclined relative to the plane defined by the widthwise direction W and the longitudinal direction L, as described later. A length of the tubular member holder 13B is preferably shorter than a length of the tubular member 30 in the longitudinal direction L. This makes it easy to take out the tubular member holder 13B from the inner case 10.

(Operation and Effect)

In the first embodiment, the heat source holder 13A holds the heat source 50 so that the predetermined direction is directed toward a direction (for example, the depth direction D) crossing the bottom surface 11A. Therefore, it is possible to easily insert the heat source 50 provided separately of the tubular member 30 into the tubular member 30.

In the first embodiment, the inner case 10 has the partition member 12 that partitions a space in the inner case 10 into the heat source housing space 10A (first space) housing the heat source 50 and the tubular member housing space 10B (second space) housing the tubular member 30. This makes it difficult for a flavor ingredient to move between the heat source 50 and the member 32 of the tubular member 30, and makes it possible to restrain the flavor inhaled by a user from deteriorating.

In the first embodiment, the heat source holder 13A has a structure to hold the heat source 50 so that the insertion end portion 50B protrudes from an upper end of the heat source holder 13A. Therefore, it is possible to more easily insert the heat source 50 into the tubular member 30.

In the first embodiment, the length with which the insertion end portion 50B of the heat source 50 protrudes from the upper end of the heat source holder 13A is approximately equal to a length with which the insertion end portion 50B of the heat source 50 should be inserted into the tubular member 30. Therefore, while the heat source 50 is held by the heat source holder 13A, when the heat source 50 is inserted into the tubular member 30, the tubular member 30 is stopped by the heat source holder 13A, and thus, it is possible to insert the heat source 50 into the tubular member 30 with an appropriate insertion length.

First Modification

A first modification of the first embodiment will be described, below. Description proceeds with a particular focus on a difference from the first embodiment, below.

Figure 7:
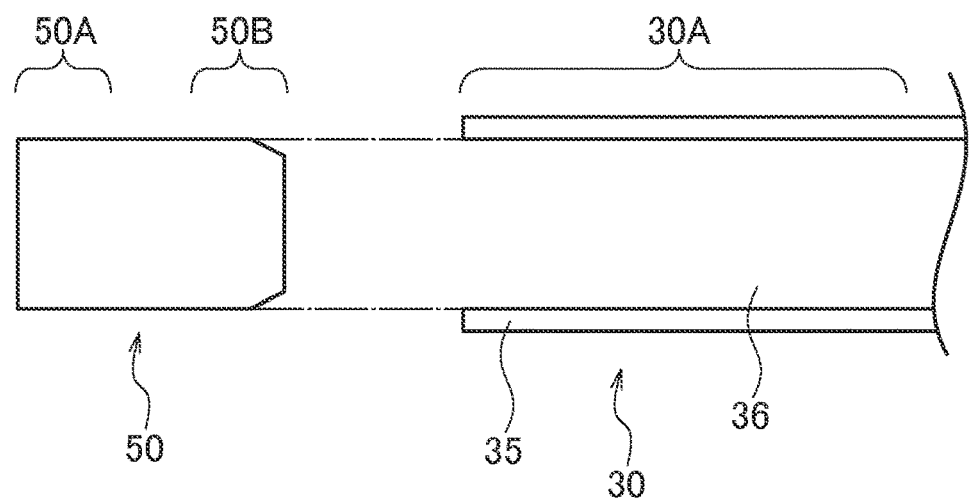
FIG. 7 is a drawing showing an insertion state of a heat source 50 according to a first modification.

In the first modification, as shown in FIG. 7, the insertion end portion 50B has a shape that an external dimension of the insertion end portion 50B decrease from the non-insertion end portion 50A toward the insertion end portion 50B. The external dimension of the insertion end portion 50B at an end of the insertion end portion 50B is smaller than an internal dimension of the supporting end portion 30A at an end of the supporting end portion 30A.

Thus, the insertion end portion 50B has such a shape that the external dimension of the insertion end portion 50B decrease from the non-insertion end portion 50A toward the insertion end portion 50B, and thus, it is easy to insert the heat source 50 into the tubular member 30. The insertion end portion 50B may have such a tapered shape that the external dimension of the insertion end portion 50B gradually changes, or may have such a shape that only an external dimension at the end of the insertion end portion 50B is small.

Second Modification

A second modification of the first embodiment will be described, below. Description proceeds with a particular focus on a difference from the first embodiment, below.

Figure 8:
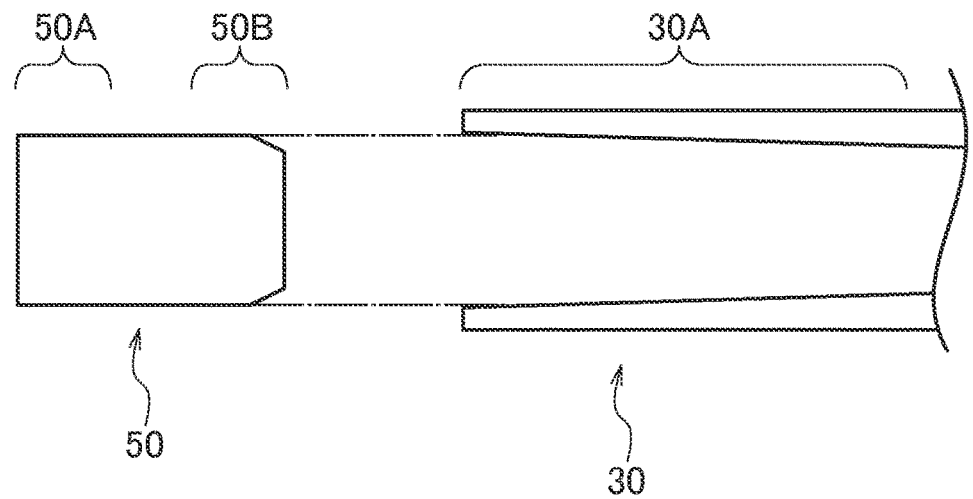
FIG. 8 is a drawing showing an insertion state of a heat source 50 according to a second modification.

In the second modification, as shown in FIG. 8, the supporting end portion 30A has a shape that an internal dimension of the supporting end portion 30A decreases from the supporting end portion 30A toward the mouthpiece side end portion 30B. The internal dimension of the supporting end portion 30A at an end of the supporting end portion 30A is larger than the external dimension of the insertion end portion 50B at an end of the insertion end portion 50B.

Thus, the supporting end portion 30A has such a shape that the internal dimension of the supporting end portion 30A decrease from the supporting end portion 30A toward the mouthpiece side end portion 30B, and thus, it is easy to insert the heat source 50 into the tubular member 30. The supporting end portion 30A may have such a tapered shape that the internal dimension of the supporting end portion 30A gradually changes, or may have such a shape that only an internal dimension at the end of the supporting end portion 30A is large.

Third Modification

A third modification of the first embodiment will be described, below. Description proceeds with a particular focus on a difference from the first embodiment, below.

Figure 9:
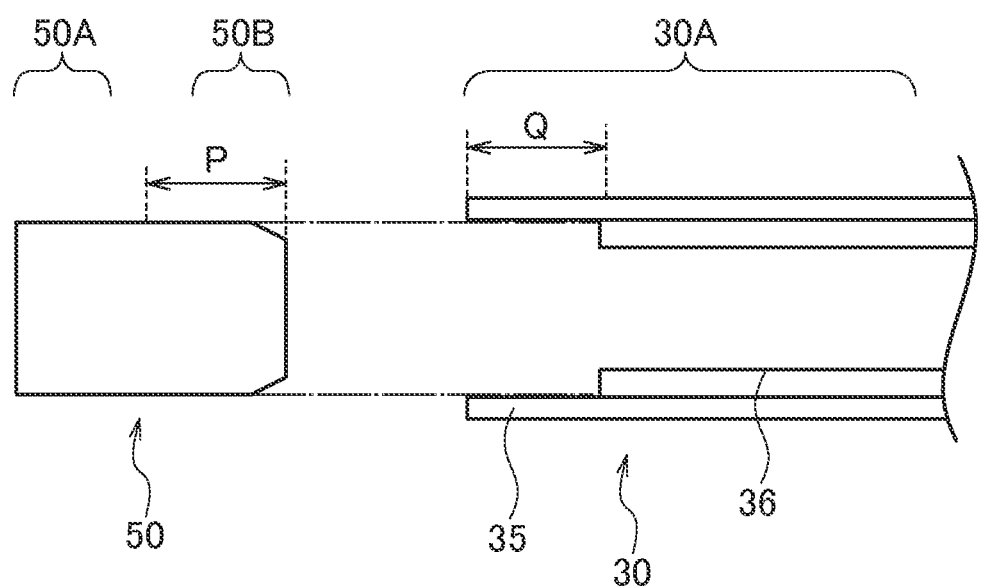
FIG. 9 is a drawing showing an insertion state of a heat source 50 according to a third modification.

In the third modification, as shown in FIG. 9, the supporting end portion 30A of the tubular member 30 is configured by an outer tubular member 35 and an inner tubular member 36. An external dimension of the insertion end portion 50B at an end of the insertion end portion 50B is approximately equal to an internal dimension of the outer tubular member 35 at an end of the outer tubular member 35. The inner tubular member 36 is provided inside the outer tubular member 35. Here, a length Q from an end of the outer tubular member 35 to an end of the inner tubular member 36 is preferably equal to a length with which the insertion end portion 50B of the heat source 50 should be inserted into the outer tubular member 35. Such a configuration allows the inner tubular member 36 to function as a regulation portion that regulates insertion of the heat source 50, and thus, it is possible to insert the heat source 50 into the outer tubular member 35 with an appropriate insertion length irrespective of a length of the insertion end portion 50B of the heat source 50 protruded from the upper end of the heat source holder 13A. Further, it is possible to insert the heat source 50 into the outer tubular member 35 with an appropriate insertion length without a need of making the outer tubular member 35 and the heat source holder 13A contact each other during insertion.

Fourth Modification

A fourth modification of the first embodiment will be described, below. Description proceeds with a particular focus on a difference from the first embodiment, below.

Figure 10:
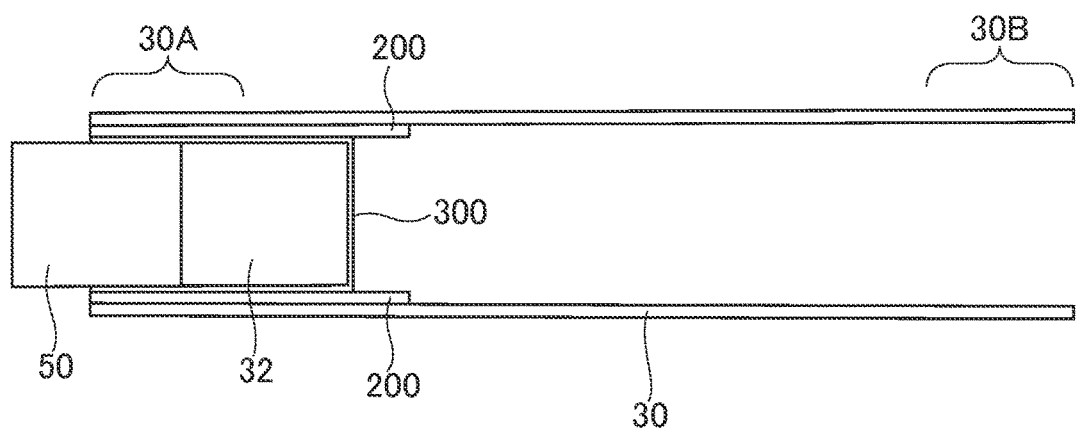
FIG. 10 is a drawing showing a flavor inhaler according to a fourth modification.
Figure 11:
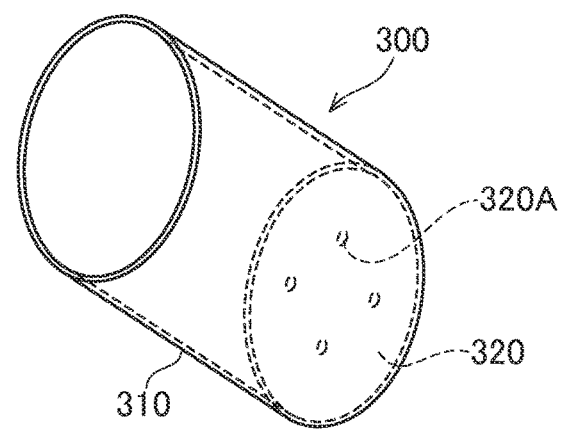
FIG. 11 is a drawing showing a cup member 300 according to the fourth modification.

Although not particularly mentioned in the first embodiment, in the fourth modification, as shown in FIG. 10, the flavor inhaler includes a heat conduction member 200 and a cup member 300 in addition to the tubular member 30 and the heat source 50.

The heat conduction member 200 is provided on an inner surface of the tubular member 30 at the supporting end portion 30A of the tubular member 30. The heat conduction member 200 is preferably formed of a metal material having an excellent heat conductivity, and is configured of aluminum, for example. The length of the heat conduction member 200 is preferably at least longer than the length of the cup member 300 in the predetermined direction. That is, the heat conduction member 200 projects toward the mouthpiece side end portion 30B side relative to the cup member 300. The length of the heat conduction member 200 may be the same as the length of the tubular member 30.

The cup member 300 has a cup shape, houses the member 32 (here, a flavor source), and holds the heat source 50. The cup member 300 is configured to be inserted into the supporting end portion 30A of the tubular member 30. In particular, the cup member 300 is configured by a tubular side wall 310 and a bottom plate 320 covering one opening configured by the side wall 310. The member 32 (here, a flavor source) and the heat source 50 are inserted into the cup member 300 from one opening configured by the side wall 310. The bottom plate 320 has a plurality of air holes 320A through which air passes.

Here, the member 32 (here, a flavor source) is configured by a powdery and granular tobacco leaf, for example. In such a case, the size of the air hole 320A is smaller than a particle diameter of the tobacco leaf.

In the fourth modification, the thickness of the side wall 310 is preferably 0.1 mm or less. As a result, a heat capacity of the side wall 310 is small, and the heat generated from the heat source 50 is efficiently transmitted to the flavor source. Further, the side wall 310 is preferably configured by SUS (for example, SUS 430). As a result, even when the thickness of the side wall 310 is 0.1 mm or less, it is possible to obtain a sufficient strength as the strength of the side wall 310 and possible to maintain the shape of the cup member 300. The bottom plate 320 is preferably configured by the same member (for example, SUS 430) as the side wall 310.

Other Embodiments

The present invention is explained through the above embodiment, but it must not be assumed that this invention is limited by the statements and the drawings constituting a part of this disclosure. From this disclosure, various alternative embodiments, examples, and operational technologies will become apparent to those skilled in the art.

In the embodiments, the package 100 (the inner case 10 and the outer case 20) has an approximately rectangular parallelepiped outer shape. However, the embodiments are not limited thereto. For example, the package 100 may be configured by a box having the heat source housing space 10A and the tubular member housing space 10B and by a lid attached to the box by a hinge, etc., in such a way as capable of opening and closing. Alternatively, the package 100 may be configured by a box having the heat source housing space 10A and the tubular member housing space 10B and by a lid provided separately of the box.

Although not particularly mentioned in the embodiments, the dimension of the package 100 in the depth direction D is preferably smaller than the dimension of the package 100 in the longitudinal direction L and the widthwise direction W. However, the embodiments are not limited thereto.

Although not particularly mentioned in the embodiments, the dimension of the package 100 in the longitudinal direction L is preferably smaller than the dimension of the package 100 in the widthwise direction W. However, the embodiments are not limited thereto.

In the embodiments, the height H1 of the heat source 50 is greater than the height H2 of the heat source holder 13A in the depth direction D. However, the embodiments are not limited thereto. The heat source holder 13A may have a structure to hold the heat source 50 so that the insertion end portion 50B protrudes from an upper end of the heat source holder 13A. Therefore, the inner case 10 may have such a structure that the bottom surface 11A rises along the depth direction D in conjunction with an operation where the inner case 10 is drawn from the outer case 20. In such a case, when the inner case 10 is drawn from the outer case 20, the heat source holder 13A holds the heat source 50 so that the insertion end portion 50B protrudes from the upper end of the heat source holder 13A.

In the embodiments, a case in which the heat source 50 is placed on the bottom surface 11 is described; however, the embodiment is not limited thereto. For example, it may be possible that a space is provided between the bottom surface 11 and the heat source 50 and that the heat source 50 is supported only by the heat source holder 13A. In such a mode, such a configuration may be possible that when the heat source 50 is inserted into the tubular member 30, the heat source 50 held by the heat source holder 13A is swung along with the insertion, and the heat source 50 contacts the bottom surface 11, or such a configuration may be also possible that a state where the space is provided between the bottom surface 11 and the heat source 50 is maintained.

In addition, the entire content of Japanese Patent Application No. 2013-47282 (filed on Mar. 8, 2013) is incorporated in the present specification by reference.

INDUSTRIAL APPLICABILITY

According to the present invention, it is possible to provide a package with which it is possible to easily insert a heat source provided separately of a tubular member into the tubular member.

The invention claimed is:

1. A package that houses at least a heat source, used for a flavor inhaler, having a columnar shape extending along a predetermined direction, comprising:
    a bottom surface; and
    a heat source holder holding the heat source so that the predetermined direction is directed toward a direction crossing the bottom surface,
    wherein the heat source holder holds the heat source provided separately of a tubular member and holds the heat source at a state that allows the heat source to swing toward the bottom surface, the tubular member, used for the flavor inhaler, having a tubular shape.

2. The package according to claim 1, comprising a partition member erected from the bottom surface, wherein
    the partition member partitions a space within the package into a first space housing the heat source and a second space housing the tubular member, and
    the heat source holder is formed in the first space.

3. The package according to claim 1, wherein
    one end portion of the heat source is a non-insertion end portion and the other end portion of the heat source is an insertion end portion inserted into the tubular member along the predetermined direction, and
    the heat source holder has a structure to hold the heat source so that the insertion end portion protrudes from an upper end of the heat source holder.

4. The package according to claim 3, wherein the insertion end portion has an inclination surface having an inclination relative to the predetermined direction.

5. The package according to claim 3, wherein a length with which the insertion end portion protrudes from the upper end of the heat source holder is approximately equal to a length with which the insertion end portion should be inserted into the tubular member.

6. The package according to claim 1, wherein the heat source is a carbon heat source.

7. The package according to claim 1, wherein the heat source is a tobacco compact.

8. The package according to claim 1, wherein
    one end portion of the tubular member is a mouthpiece side end portion provided at a mouthpiece side and the other end portion of the tubular member is a supporting end portion that supports the heat source, and
    the supporting end portion has a shape that an internal dimension of the supporting end portion decreases from the supporting end portion toward the mouthpiece side end portion.

9. The package according to claim 1, wherein
    one end portion of the heat source is a non-insertion end portion and the other end portion of the heat source is an insertion end portion inserted into the tubular member along the predetermined direction,
    one end portion of the tubular member is a mouthpiece side end portion provided at a mouthpiece side and the other end portion of the tubular member is a supporting end portion that supports the heat source, and
    an inner wall of the supporting end portion has a regulation portion that regulates insertion of the insertion end portion along the predetermined direction.

10. The package according to claim 1, wherein the package further houses the tubular member.

\* \* \* \* \*